(12) United States Patent
Barber et al.

(10) Patent No.: US 9,790,109 B2
(45) Date of Patent: Oct. 17, 2017

(54) METHOD FOR SANITIZING AN ELECTRODEIONIZATION DEVICE

(75) Inventors: John Harold Barber, Fergus (CA); Wojciech Gutowski, Hamilton (CA)

(73) Assignee: General Electric Company, Schenectady, NY (US)

(*) Notice: Subject to any disclaimer, the term of this patent is extended or adjusted under 35 U.S.C. 154(b) by 1763 days.

(21) Appl. No.: 12/771,597

(22) Filed: Apr. 30, 2010

(65) Prior Publication Data

US 2011/0266216 A1    Nov. 3, 2011

(51) Int. Cl.
| | | |
|---|---|---|
| *B01D 65/02* | (2006.01) |
| *A61L 2/00* | (2006.01) |
| *C02F 1/469* | (2006.01) |
| *A61L 2/03* | (2006.01) |
| *A61L 2/04* | (2006.01) |
| *C02F 9/00* | (2006.01) |

(52) U.S. Cl.
CPC ............ *C02F 1/4695* (2013.01); *A61L 2/035* (2013.01); *A61L 2/04* (2013.01); *C02F 9/00* (2013.01); *C02F 2303/04* (2013.01); *C02F 2303/14* (2013.01)

(58) Field of Classification Search
CPC ........................... B01J 49/0056; C02F 1/4695
USPC .................... 210/636, 900; 422/22
See application file for complete search history.

(56) References Cited

U.S. PATENT DOCUMENTS 2,423,598 A * 7/1947 Hynes ............................ 392/460
4,184,948 A * 1/1980 Dabby et al. ................ 210/662
6,149,788 A   11/2000 Tessier et al.
(Continued)

FOREIGN PATENT DOCUMENTS

CN      101160264 A    4/2008
JP      2001029752 A    2/2001
(Continued)

OTHER PUBLICATIONS

Electrochemical Devices ("Aqueous Anodes," pub. By electrochemical devices, inc., Main Office at Albion, RI, 1998, accessed on the Internet at http://www.edi-cp.com/pdf/aqueous_anodes.pdf, on Apr. 18, 2014).*
PCT Search Report and Written Opinion Issued in PCT/US2011/033044 Jun. 6, 2011.
(Continued)

*Primary Examiner* — Bobby Ramdhanie
*Assistant Examiner* — Denise R Anderson

(57) ABSTRACT

The present invention has the technical effect of disinfecting an EDI device of a water purification system. The present invention may be applied to an EDI device having an internal chamber comprising ion exchange components. The internal chamber may also comprise a plurality of ion selective membranes positioned between the anode and the cathode compartments. As illustrated and described herein, embodiments of the present invention seek to sanitize the EDI device without sanitization chemicals or a water supply. Embodiments of the present invention disinfect the EDI device by applying electrical power. Here an electrical supply device heats the EDI device, through resistive heating of the internal chambers, to a sanitization temperature. The resistive heating is a result of ionic movement through the internal chamber. The friction that is created through the ionic movement increases the temperature within the internal chamber.

20 Claims, 3 Drawing Sheets

(56) References Cited

U.S. PATENT DOCUMENTS

| | | |
|---|---|---|
| 6,461,512 B1 | 10/2002 | Hirayama et al. |
| 6,823,878 B1 | 11/2004 | Gadini |
| 7,147,785 B2 | 12/2006 | Arba et al. |
| 2002/0144954 A1 | 10/2002 | Arba et al. |
| 2005/0263457 A1 | 12/2005 | Wilkins et al. |
| 2007/0108056 A1 | 5/2007 | Nyberg et al. |

FOREIGN PATENT DOCUMENTS

| | | | | |
|---|---|---|---|---|
| JP | 2002126744 A | | 5/2002 | |
| JP | 2004074109 A | * | 3/2004 | ............... A61L 2/04 |
| JP | 2005254200 A | | 9/2005 | |
| JP | 2005254201 A | | 9/2005 | |
| JP | 2005288335 A | | 10/2005 | |
| JP | 2007075712 A | | 3/2007 | |
| JP | 2007252396 A | | 10/2007 | |
| TW | 417778 U | | 1/2001 | |

OTHER PUBLICATIONS

A Copy of Chinese Office Action issued in connection with corresponding CN Application No. 201180021887.7 on Aug. 5, 2013.
A Copy of Japanese Office Action issued in connection with corresponding JP Application No. 2013508032 on Jan. 27, 2015.
A Copy of Taiwan Office Action issued in connection with corresponding TW Application No. 100115221on Aug. 13, 2015.
A Copy of Japanese Office Action issued in connection with corresponding JP Application No. 2013508032 on Oct. 27, 2015.
Unofficial English translation of Japanese Notice of Allowance issued in connection with corresponding JP Application No. 2013508032 on Feb. 16, 2016.

* cited by examiner

METHOD FOR SANITIZING AN ELECTRODEIONIZATION DEVICE

BACKGROUND OF THE INVENTION

The present invention relates to a water purification system that incorporates an electrodeionization (EDI) device; and more particularly to a method of sanitizing the EDI device.

Electrodeionization generally refers to a process for purifying liquids by combining ion exchange resins, ion exchange membranes, and electricity to purify the liquids. The use of water purification systems has increased in many industries. In particular, pure water is used in many industrial processes. Some of these processes include: producing semiconductor chips, power plant operations, petrochemical applications and producing pharmaceuticals. Ion exchange resins, reverse osmosis (RO) filtration, and electrodialysis techniques have been used to reduce the concentration of ions in a liquid. EDI devices are now commonly used as RO post treatment to reduce the concentration of ions producing ultra-pure water.

An EDI device generally includes an internal chamber, within which alternating arrangements of cation permeable membranes and anion permeable membranes define compartments. The diluting compartments contain ion exchange resin particles, which are regenerated through electric field induced water dissociation. The concentrate compartments may contain ion exchange particles or inert plastic netting to maintain membrane separation, and allow water flow. An applied electric current induces ion migration from the diluting compartments through the ion exchange media and ion permeable membranes into the concentrating compartments. The liquid flowing through the concentrating compartments is discarded or partially recycled. The purified liquid flowing through the diluting compartments is recovered as demineralized liquid product.

Operation of the water purification system infects the EDI device with bacteria and other undesirable substances. A sanitization process is used to disinfect the EDI device. Some disinfecting methods involve passing a disinfecting solution, which may include a chemical, at a temperature sufficient to inactivate any microorganisms in the EDI device.

There are a few issues with known methods of disinfecting the EDI device. Known methods require external equipment (water supply, heating means, etc) to disinfect the EDI device. Chemical disinfecting solutions may contain chemicals that react with the active components in the EDI device. This may lead to component degradation and the decrease of the usable life of the EDI device. These issues add to the cost and complexity of the water purification system.

For the foregoing reasons, there is a desire for an improved method of disinfecting an EDI device. The method should reduce the need for external equipment and disinfecting chemicals.

BRIEF DESCRIPTION OF THE INVENTION

In accordance with an embodiment of the present invention, a method of sanitizing an electrodeionization (EDI) device, the method comprising: providing an EDI device comprising an internal chamber comprising: an anode compartment adjacent a first end of the internal chamber, a cathode compartment adjacent an opposite second end of the internal chamber, and a plurality of ionic membranes positioned between the anode and the cathode compartments; stopping a fluid supply to the internal chamber; supplying an electrical power across the anode and the cathode compartments until a temperature within the internal chamber is within a sanitization range; and controlling the electrical power to maintain the temperature within the internal chamber within a sanitization range; wherein the elevated temperature produced by the electrical power sanitizes the EDI device while the fluid supply is minimized.

In accordance with an alternate embodiment of the present invention, a method of sanitizing an electrodeionization (EDI) device associated with a deionized water producing system, the method comprising: providing a water purification system configured for producing deionized water, the water purification system comprising at least one of: a micro-filtration apparatus, an activated carbon tower, or a reverse osmosis apparatus; providing an EDI device, integrated with the water purification system, wherein the EDI device comprises an internal chamber comprising: an anode compartment adjacent a first end of the internal chamber, a cathode compartment adjacent an opposite second end of the internal chamber, and a plurality of ionic membranes positioned between the anode and the cathode compartments; modulating an isolation valve to stop a fluid supply to the internal chamber; supplying an electrical power to the internal chamber to create a temperature rise with the internal chamber; determining whether a temperature within the internal chamber is within a sanitization range; and maintaining the temperature within the sanitization range; wherein the electrical power sanitizes the EDI device.

DETAILED DESCRIPTION OF THE INVENTION

The present invention has the technical effect of disinfecting an EDI device of a water purification system. The present invention may be applied to an EDI device having an internal chamber comprising ion exchange components. The ion exchange components may include, but are not limited to, an anode compartment adjacent a first end of the internal chamber, a cathode compartment adjacent an opposite second end. The internal chamber may also comprise a plurality of ion selective membranes positioned between the anode and the cathode compartments. As illustrated and described herein, embodiments of the present invention seek to sanitize the EDI device without the use of sanitization chemicals or a secondary hot water supply.

Figure 1:
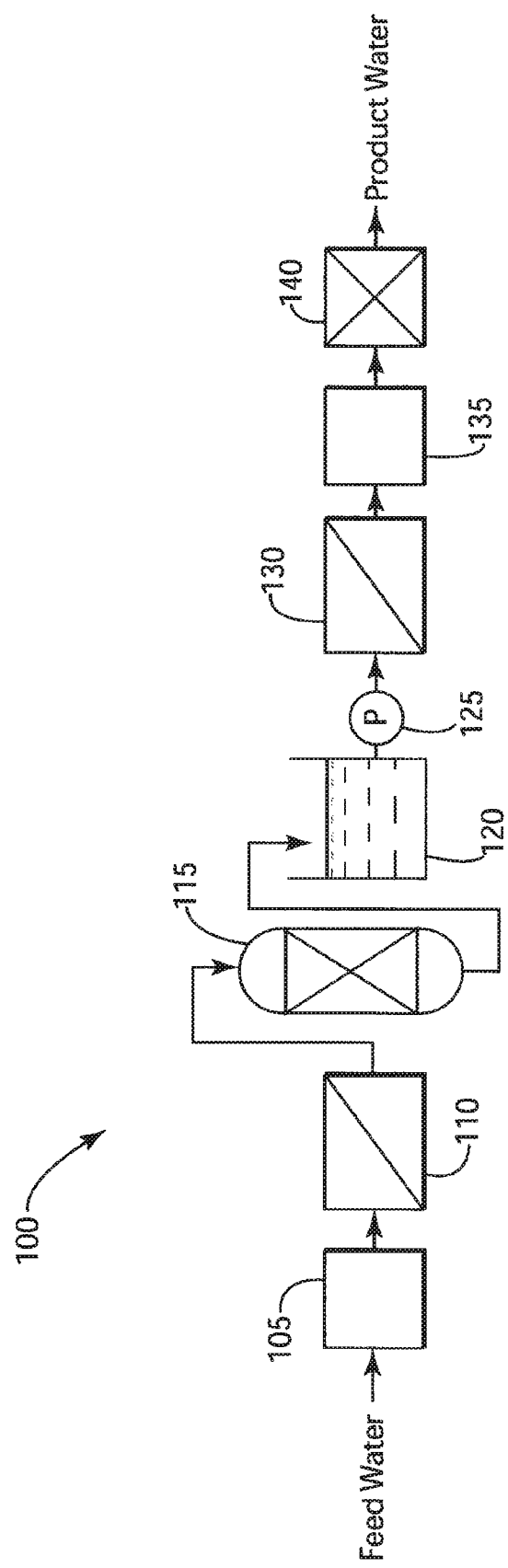
FIG. 1 is a schematic illustrating a known water purification system.
Figure 2:
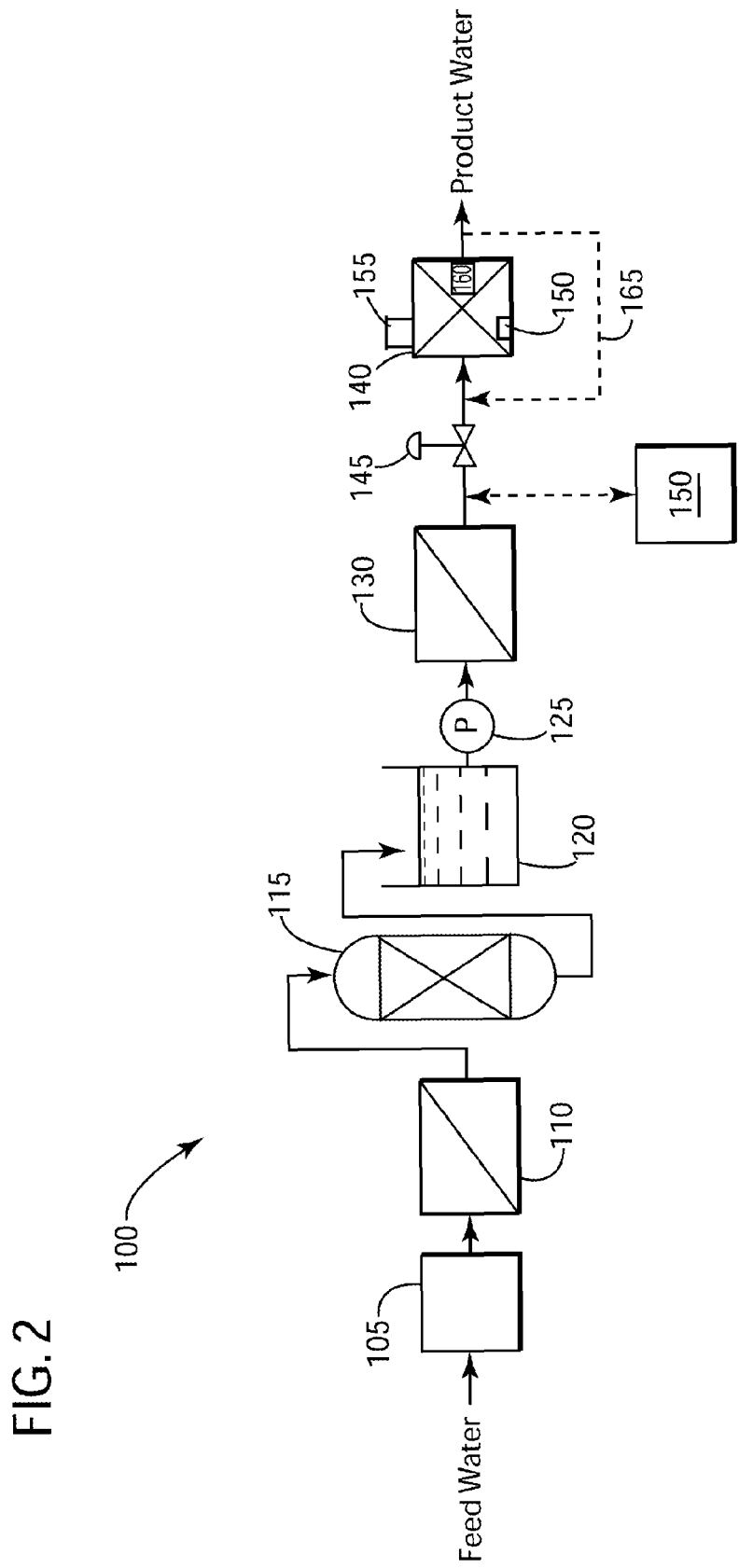
FIG. 2 is a schematic illustrating a water purification system, in accordance with an embodiment of the present invention.

Detailed example embodiments are disclosed herein. However, specific structural and functional details disclosed herein are merely representative for purposes of describing example embodiments. Example embodiments may, however, be embodied in many alternate forms, and should not be construed as limited to only the embodiments set forth herein. For example, but not limiting of, the water purification system 100, as illustrated in FIGS. 1 and 2, comprise the following components: a heat exchanger 105; a micro-filtration apparatus 110; an activated carbon tower 115; a tank 120; a pump 125; a reverse-osmosis apparatus 130; and an EDI device 140. Embodiments of the present invention are not intended to be limited to a water purification system 100 comprising all of those components. Indeed, embodiments of the present invention may be applied to other water purification systems 100 comprising more or less than the aforementioned components.

Accordingly, while example embodiments are capable of various modifications and alternative forms, embodiments thereof are illustrated by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any, and all, combinations of one or more of the associated listed items.

Referring now to the FIGS., where the various numbers represent like elements throughout the several views, FIG. 1 is a schematic illustrating a known water purification system 100. FIG. 1 may be considered a non-limiting example of a known configuration of a water purification system 100. Feedwater enters the heat exchanger 105 and is treated by the micro-filtration (MF) apparatus 110 and then by the activated carbon (AC) tower 115. Next, the feedwater is fed from the tank 120 to the reverse osmosis (RO) apparatus 130 via the pump 125. If required, the permeated water from the RO apparatus 130 is conditioned by the heat exchanger 135. Next, the feedwater is treated by the EDI device 140.

A known method of sanitizing the water purification system 100 may involve the following steps. First, for disinfecting purposes, hot water of around 175 Degrees Fahrenheit may flow from the heat exchanger 105 to the RO apparatus 130 via the MF apparatus 110, the tower 115, the tank 120, and the pump 125.

Next, the EDI device 140 is disinfected. Here, water at an ambient temperature flows through the heat exchanger 105, the MF apparatus 110, the tower 115, the tank 120, the pump 125, the RO apparatus 130, the heat exchanger 135, and the EDI device 140. The heat exchanger 135 heats the ambient water at a specified rate until the temperature reaches around 175 Degrees Fahrenheit, as the water exits the diluting compartment of the EDI device 140. Next, the hot water flows through the EDI device 140 for a designated soak time. Next, the hot water is cooled at designated rate until the temperature at the outlet of the diluting compartment is around 95 Degrees Fahrenheit.

FIG. 2 is a schematic illustrating a water purification system 100, in accordance with an embodiment of the present invention. Embodiments of the present invention provide a system for disinfecting the EDI device 140, without the use of a heated water supply and/or chemicals. The majority of the components of the water purification system 100 may be the same or similar to those illustrated in FIG. 1. For comparison purposes, the discussion of FIG. 2 will focus on the aspects and the features of the present invention. As illustrated in FIG. 2, embodiments of the present invention do not require the heat exchanger 135 to heat water for use in disinfecting the EDI device 140. As described below, an isolation valve 145 stops the water supply flowing into the EDI device 140 while the disinfecting process is performed.

Embodiments of the present invention use electrical power to disinfect the EDI device 140. Here, an electrical supply device 160 may use resistive heating to heat the internal chambers of the EDI device 140. The heating may occur until the internal chambers reach a sanitization temperature.

The resistive heating is a result of the ionic movement through the internal chamber. The friction that is created through the ionic movement increases the temperature within the internal chamber. As the temperature of the internal chamber increases, the viscosity of the fluid therein decreases, the friction also decreases, and the ionic movement increases. This, along with other water splitting phenomena, may result in an overall decrease in the electrical resistance of the EDI device 140. Given the proportional relationship between voltage (V) and the product of current (I) and resistance (R), $V=I*R$, the following non-limiting example demonstrates the effect of the heating of the internal chamber, in an embodiment of the present invention.

Initially, the temperature of the internal chamber is around 20 Degrees Centigrade, and the voltage around 150 Volts.

A constant current is applied and the voltage becomes an indication of the resistance.

The voltage decreases to around 100 Volts when the water within the internal chamber is in the sanitization temperature range.

Thus, the voltage drop across the EDI device 140 may be monitored to determine whether the internal chamber is within the sanitization range.

Temperature devices, such as, but not limiting of, thermocouples, resistance temperature detectors (RTDs), or the like, may also determine when the sanitization temperature has been reached. A first embodiment of the temperature device may comprise an external temperature device 155, which may determine the temperature on a surface outside of the EDI device 140. This may be considered the skin temperature and may correlate to temperature within the internal chamber. A second embodiment of the temperature device may comprise internal temperature device 150, which may determine the temperature inside the internal chamber. A third embodiment of the temperature device may comprise a device that measures a temperature of the water within the internal chamber, which correlates to the temperature inside of the internal chamber.

After the internal chamber maintains the sanitization temperature for a soak time, a rinse may be performed to remove collected organic and inorganic impurities from the EDI device 140.

In an alternate embodiment of the present invention, a recirculation system 165 may be integrated with the EDI device 140. This feature may increase the efficiency of the sanitization process. In an embodiment of the recirculation system 165, the discharge flowing through an outlet of the EDI device 140 is returned to an inlet of the EDI device 140.

In another alternate embodiment of the present invention, the EDI device 140 may serve as the primary heat source for sanitizing the water purification system 100. For example, but not limiting of, the water exiting an outlet of the EDI system 100 may be within the sanitization range. This water may be circulated through components of the water purification system 100 which require sanitization.

Depending on the size and complexity of the water purification system 100, the available heat from the EDI device 140 may be inadequate to sanitize some components. Here, the embodiments of the present invention may allow for integration with a booster heater 170 or the like. This may comprise the form of a preexisting external heat source, a new external heat source, or combination thereof. In use, the EDI device 140 may serve as the primary heat source and the booster heater 170 as the secondary; which collectively operate to provide sufficient heat to sanitize the components of the water purification system 100.

Figure 3:
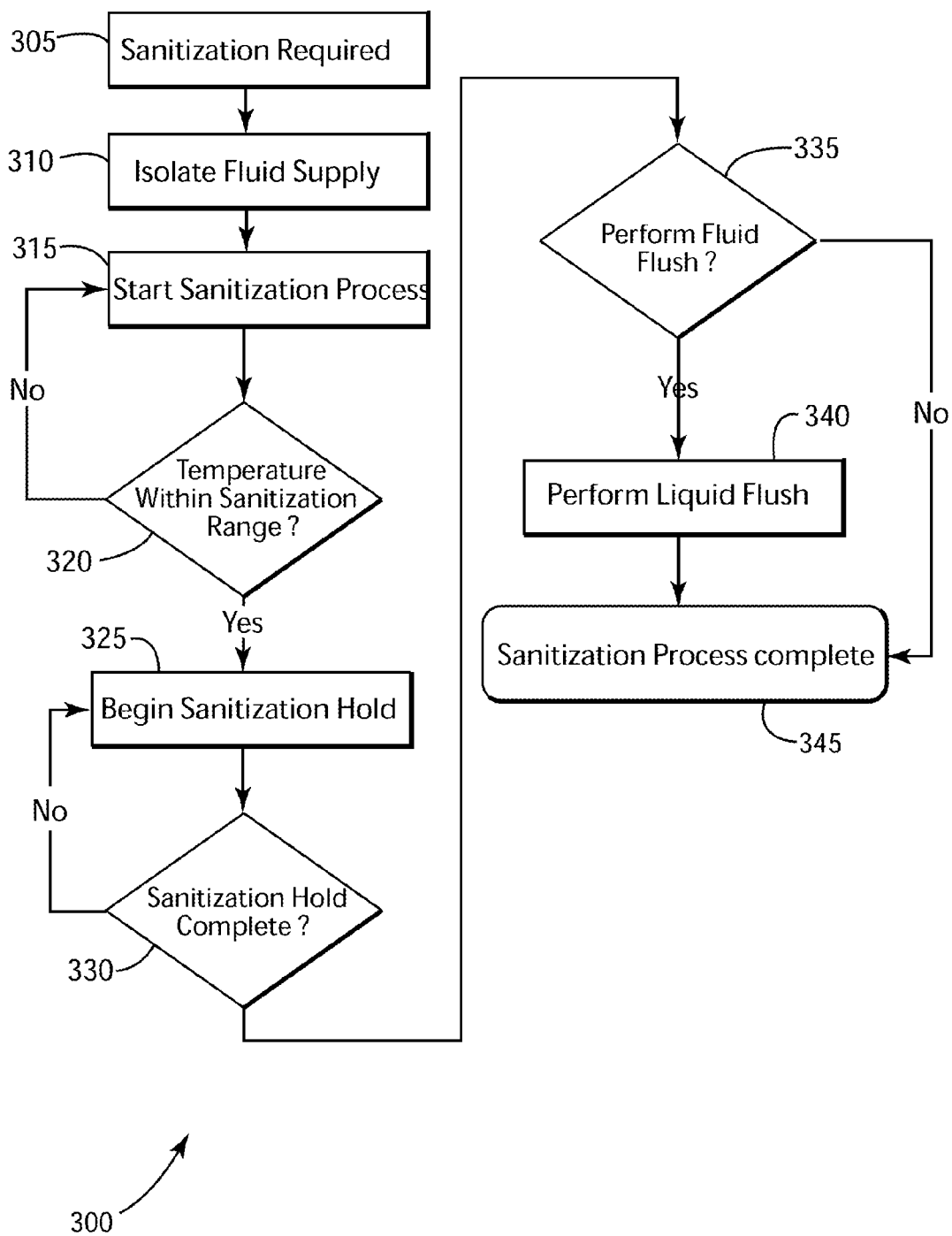
FIG. 3 is a flowchart illustrating a method of disinfecting an EDI device, in accordance with an embodiment of the present invention.

FIG. 3 is a flowchart illustrating a method 300 of disinfecting an EDI device, in accordance with an embodiment of the present invention. The steps of the method 300 may be performed manually; automatically via a control system, or the like; or via a combination of manual and automatic steps. The following discussion focuses on an application where the steps of the method 300 are automatically performed via a control system, or the like.

As will be appreciated, the present invention may be embodied as a method, system, or computer program product. Accordingly, the present invention may take the form of an entirely hardware embodiment, an entirely software embodiment (including firmware, resident software, microcode, etc.) or an embodiment combining software and hardware aspects all generally referred to herein as a "circuit", "module," or "system". Furthermore, the present invention may take the form of a computer program product on a computer-usable storage medium having computer-usable program code embodied in the medium. As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are exemplary only, and are thus not limiting as to the types of memory usable for storage of a computer program. Any suitable computer readable medium may be utilized.

The computer-usable or computer-readable medium may be, for example but not limited to, an electronic, magnetic, optical, electromagnetic, infrared, or semiconductor system, apparatus, device, or propagation medium. More specific examples (a non exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

The term processor, as used herein, refers to central processing units, microprocessors, microcontrollers, reduced instruction set circuits (RISC), application specific integrated circuits (ASIC), logic circuits, programmable logic controllers (PLCs), and any other circuit or processor capable of executing the functions described herein.

Computer program code for carrying out operations of the present invention may be written in an object oriented programming language such as Java7, Smalltalk or C++, or the like. However, the computer program code for carrying out operations of the present invention may also be written in conventional procedural programming languages, such as the "C" programming language, or a similar language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatuses (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a public purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory. These instructions can direct a computer or other programmable data processing apparatus to function in a particular manner. This is such that the instructions stored in the computer-readable memory produce an article of manufacture including instruction means which implement the function/act specified in the flowchart and/or block diagram block or blocks. The computer program instructions may also be loaded onto a computer or other programmable data processing apparatus. These instructions may cause a series of operational steps to be performed on the computer or other programmable apparatus to produce a computer implemented process. Here, the instructions, which execute on the computer or other programmable apparatus, provide steps for implementing the functions/acts specified in the flowchart and/or block diagram blocks.

In step 305, the method 300 may have determined that a sanitization of the EDI device is required. There are many ways to determine when the EDI device requires sanitization. These include, but are not limited to, a time interval, schedule, of the like; or measuring the level of bioactivity in the water purification system; or a decrease in performance; or inspection of EDI device components.

Referring again to FIG. 3, in step 310, the method 300 may isolate the fluid supply to the EDI device. Here an isolation valve, or the like, may be modulated in a manner that restricts the flow of fluid into the EDI device.

In step 315, the method 300 may start the sanitization process. Here, the EDI device may be substantially drained of fluid present within the internal chamber. Then, an electrical supply device provides electrical power across the anode and cathode compartments of the internal chamber. The electrical power is controlled such that the temperature within the internal chamber reaches a sanitization range. Here, the electrical power may be in the form of current flowing through the components of the internal chamber. In an embodiment the present invention, the magnitude of the current may have a range of up to about 20 milliamperes per squared centimeter.

In step 320, the method 300 may determine whether the temperature within the internal chamber is within a sanitization range. In an embodiment of the present invention, temperature rise within the internal chamber may be from about 120 degrees Fahrenheit to about 212 degrees Fahrenheit. Embodiments of the present invention may use a temperature device to determine the temperature within the internal chamber; as described. If the temperature is within the sanitization range, then the method 300 may proceed to step 325; otherwise the method 300 may revert to step 315 where the electrical supply device may be controlled in a manner that increases the temperature of the internal chamber.

In step 325, the method 300 may begin a sanitization hold, which may be considered a soak time, or the like. The length of the sanitization hold may relate, in part, to the sanitization temperature. A higher sanitization temperature may require a shorter hold time, and vice-versa. In an embodiment of the present invention the hold time may comprise a range of from about one hour to about six hours.

In step 330, the method 300 may determine whether a sanitization hold is complete. Here, the method 300 may determine if the hold time has elapsed. If the sanitization hold is complete, then the method may proceed to step 335; otherwise the method may revert to step 325.

In step 335, the method may determine whether a water flush should be performed. A flush may remove collected organic and inorganic impurities produced during the sanitization from the EDI device. A flush may also cool the components of the internal chamber. Generally, the flush may be performed until the TOC discharge, discharge temperature, or discharge product resistivity is within an acceptable range. If a flush is to be performed, then the method 300 may proceed to step 340; otherwise the method may proceed to step 345.

In step 340, the method 300 may perform the flush. The isolation valve may be modulated to a position that allows fluid, such as, but not limiting of, water, to enter the internal chamber. In an embodiment of the present invention a user may determine the duration of flush. A user may also determine the physical parameters (temperature, pressure, flowrate) of the fluid performing the flush.

In step 345, the method 300 may be considered complete. Here, the water purification system may be ready for regular operation, or the like.

The flowcharts and step diagrams in the FIGS. illustrate the architecture, functionality, and operation of possible implementations of systems, methods and computer program products according to various embodiments of the present invention. In this regard, each step in the flowchart or step diagrams may represent a module, segment, or portion of code, which comprises one or more executable instructions for implementing the specified logical function(s). It should also be noted that, in some alternative implementations, the functions noted in the step may occur out of the order noted in the figures. For example, two steps shown in succession may, in fact, be executed substantially concurrently, or the steps may sometimes be executed in the reverse order, depending upon the functionality involved. It will also be noted that each step of the block diagrams and/or flowchart illustration, and combinations of steps in the block diagrams and/or flowchart illustration, can be implemented by special purpose hardware-based systems which perform the specified functions or acts, or combinations of special purpose hardware and computer instructions.

As one of ordinary skill in the art will appreciate, the many varying features and configurations described above in relation to the several exemplary embodiments may be further selectively applied to form the other possible embodiments of the present invention. Those in the art will further understand that all possible iterations of the present invention are not provided or discussed in detail, even though all combinations and possible embodiments embraced by the several claims below or otherwise are intended to be part of the instant application. In addition, from the above description of several exemplary embodiments of the invention, those skilled in the art will perceive improvements, changes, and modifications. Such improvements, changes, and modifications within the skill of the art are also intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

What is claimed is:

1. A method of sanitizing an electrodeionization (EDI) device, the method comprising:
    providing an EDI device comprising an internal chamber comprising: an anode compartment adjacent a first end of the internal chamber, a cathode compartment adjacent an opposite second end of the internal chamber, and a plurality of ionic membranes positioned between the anode and the cathode compartments;
    stopping a fluid supply to the internal chamber;
    supplying an electrical power across the anode and the cathode compartments until a temperature within the internal chamber is within a sanitization range; and
    controlling the electrical power to maintain the temperature within the internal chamber within a sanitization range;
    wherein the electrical power sanitizes the EDI device while the fluid supply is reduced.

2. The method of claim 1, wherein the step of controlling the electrical power to maintain the temperature further comprises determining whether a sanitization hold is complete.

3. The method of claim 2 further comprising the step of flushing the internal chamber after the sanitization hold is complete.

4. The method of claim 1, wherein the step of supplying the electrical power results in a temperature rise within the internal chamber of from about 120 degrees Fahrenheit to about 212 degrees Fahrenheit.

5. The method of claim 2, wherein an interval for the sanitization hold comprises a range of from about 15 minutes to about six hours.

6. The method of claim 1, wherein the electrical power comprises the form of current flowing into the internal chamber.

7. The method of claim 6, wherein a current density comprises a range of up to about 20 milliamperes per squared centimeter.

8. The method of claim 1 further comprising the step of a using a temperature device to determine the temperature within the internal chamber.

9. The method of claim 8, wherein the temperature device is located within the internal chamber; and determines the temperature within the internal chamber.

10. The method of claim 8, wherein the temperature device measures a temperature of the fluid within the internal chamber.

11. The method of claim 8, wherein the temperature device is located external to the internal chamber; and determines a skin temperature located on an external surface of the EDI device.

12. The method of claim 6 further comprising monitoring a voltage of the EDI device to determine if the internal chamber is within the sanitization range.

13. The method of claim 1 further comprising recirculating the fluid within the chamber.

14. The method of claim 1 further comprising the step of providing a water purification system configured for producing deionized water, the water purification system comprising at least one of: a micro-filtration apparatus, an activated carbon tower, or a reverse osmosis apparatus; wherein the EDI device is integrated within the water purification system.

15. A method of sanitizing an electrodeionization (EDI) device associated with a deionized water producing system, the method comprising:
   providing a water purification system configured for producing deionized water, the water purification system comprising at least one of a micro-filtration apparatus, an activated carbon tower, or a reverse osmosis apparatus;
   providing an EDI device, integrated with the water purification system, wherein the EDI device comprises an internal chamber comprising: an anode compartment adjacent a first end of the internal chamber, a cathode compartment adjacent an opposite second end of the internal chamber, and a plurality of ionic membranes positioned between the anode and the cathode compartments;
   modulating an isolation valve to stop a fluid supply to the internal chamber;
   supplying an electrical power to the internal chamber to create a temperature rise with the internal chamber;
   determining whether a temperature within the internal chamber is within a sanitization range; and
   maintaining the temperature within the sanitization range;
   wherein the electrical power sanitizes the EDI device while the fluid supply to the internal chamber is substantially reduced.

16. The method of claim 15 further comprising the step of determining whether a sanitization hold is complete.

17. The method of claim of claim 16 further comprising the step of flushing the internal chamber after the sanitization hold is complete.

18. The method of claim 15 further comprising the step of utilizing the EDI device to sanitize the water purification system.

19. The method of claim 18 further comprising the steps of:
   a. modulating the isolation valve to allow the fluid supply to flow into the internal chamber;
   b. discharging the fluid from the internal chamber; and
   c. recirculating the fluid through the water purification system.

20. The method of claim 19 further comprising providing a booster heater to assist with heating and maintaining the fluid supply to within the sanitization range.

* * * * *